US011633532B2

(12) United States Patent
Chen

(10) Patent No.: US 11,633,532 B2
(45) Date of Patent: Apr. 25, 2023

(54) DEVICE FOR PROMOTING WOUND HEALING BY HIGH POLYMER LOW TEMPERATURE IONIZED GAS

(71) Applicant: ROSACE INTERNATIONAL CO., LTD., Taipei (TW)

(72) Inventor: Kuo-Kang Chen, Taipei (TW)

(73) Assignee: Rosace International Co., Ltd., Taipei (TW)

( * ) Notice: Subject to any disclaimer, the term of this patent is extended or adjusted under 35 U.S.C. 154(b) by 387 days.

(21) Appl. No.: 17/114,938

(22) Filed: Dec. 8, 2020

(65) Prior Publication Data
US 2022/0176023 A1    Jun. 9, 2022

(51) Int. Cl.
| | |
|---|---|
| *B01D 46/10* | (2006.01) |
| *A61M 1/00* | (2006.01) |
| *A61M 1/34* | (2006.01) |
| *B01D 46/00* | (2022.01) |
| *B01D 53/26* | (2006.01) |
| *B01D 53/04* | (2006.01) |

(52) U.S. Cl.
CPC ............... *A61M 1/85* (2021.05); *A61M 1/34* (2013.01); *B01D 46/0012* (2013.01); *B01D 46/10* (2013.01); *B01D 53/04* (2013.01); *B01D 53/261* (2013.01); *A61M 2202/0266* (2013.01); *A61M 2205/0211* (2013.01); *A61M 2205/3317* (2013.01); *A61M 2205/3633* (2013.01); *B01D 2253/308* (2013.01); *B01D 2256/12* (2013.01); *B01D 2259/4533* (2013.01); *H05H 2245/34* (2021.05); *Y10S 95/902* (2013.01)

(58) Field of Classification Search
CPC .................. A61B 18/042; A61B 34/30; A61B 2018/00023; A61B 2018/00452; A61B 2562/0257; A61B 2018/00744; A61B 2018/00898; A61B 2018/00642; A61L 2/14; A61L 2/0011; A61M 1/34; A61M 35/30; A61M 1/85; A61M 2205/3317; A61M 2202/0266; A61M 2205/0211; A61M 2205/3633; B01D 53/261; B01D 53/04; B01D 46/0012; B01D 46/10; B01D 2253/308; B01D 2256/12; B01D 2259/4533; H05H 2245/34; Y10S 95/902
See application file for complete search history.

(56) References Cited

U.S. PATENT DOCUMENTS 8,764,701 B1 * 7/2014 Hicks .................. A61B 18/042
604/23

* cited by examiner

*Primary Examiner* — Sharon Pregler
(74) *Attorney, Agent, or Firm* — Rosenberg, Klein & Lee

(57) ABSTRACT

A device has a power source having a high voltage terminal and a low voltage terminal, an oil-free gas compressor, a first molecular sieve, multiple ionized gas generators, an outer metal pipe, an inner metal pipe, a dielectric insulating ceramic sheet, and a gas outlet pipe. The first molecular sieve is connected between the oil-free gas compressor and the ionized gas generators, and is capable of filtering out molecules in the gas except for oxygen. The outer metal pipe and the inner metal pipe are electrically connected to the low voltage terminal and the high voltage terminal respectively. The dielectric insulating ceramic sheet is mounted between the outer metal pipe and the inner metal pipe, and forms an ionizing space, which communicates with the ionizing space, with the outer metal pipe.

10 Claims, 2 Drawing Sheets

DEVICE FOR PROMOTING WOUND HEALING BY HIGH POLYMER LOW TEMPERATURE IONIZED GAS

BACKGROUND OF THE INVENTION

1. Field of the Invention

The present invention relates to a device, especially to a device that is capable of generating high polymer low temperature ionized gas to promote wound healing.

2. Description of the Prior Arts

A conventional wound treatment process for skin trauma is as follows. First, the wound is cleaned and disinfected. Then, the wound is dressed with medicine and covered with medical gauze, wherein the dressing will be changed regularly. Finally, medical supplies such as an artificial skin will be applied to the wound to promote wound healing and to avoid scars.

However, the abovementioned wound treatment process has the following disadvantages.

First, it will take a long time to heal the wound by dressing the wound with medicine and covering the wound with medical gauze, and the wound will be exposed to the risk of secondary infection during change of dressing.

Second, under gauze coverage, tissue fluid from the wound might stick to the medical gauze and then solidify and scab, such that the medical gauze should be torn off from the wound before change of the dressing. In this way, it will not only cause pain and discomfort to the injured, but also damage the scabbed wound and cause a new wound.

Third, although the abovementioned wound treatment process heals the wound, elasticity of the newly generated skin on the healed wound will be significantly reduced, and further leads to the mobility inconvenience for the injured. Wherein, elasticity of normal skin is about 145%, while the elasticity of the newly grown skin on the healed wound can only reach 100%.

To overcome the shortcomings, the present invention provides a device to mitigate or obviate the aforementioned problems.

SUMMARY OF THE INVENTION

The main objective of the present invention is to provide a device that is capable of generating high polymer low temperature ionized gas to promote wound healing. Herein, high polymer is defined as reactive gas molecule produced by low pressure reaction of atmospheric plasma. The device is capable of generating ion gas and forming a nitrogen-containing heterocyclic compound, and is capable of blowing the ion gas and the nitrogen-containing heterocyclic compound to the wound via pressure to make the ion gas and the nitrogen-containing heterocyclic compound contact the wound to cause Bohr Effect on the wound. Therefore, sebaceous membrane will be generated on the wound to quickly heal the wound, and this will be helpful to naturally restore skin elasticity.

The device for generating high polymer low temperature ionized gas to promote wound healing has a power source, an oil-free gas compressor, a first molecular sieve, and multiple ionized gas generators. The power source has a high voltage terminal and a low voltage terminal. The oil-free gas compressor generates gas with pressure. The first molecular sieve is connected to the oil-free gas compressor. The first molecular sieve is capable of filtering out molecules in the gas generated by the oil-free gas compressor except for oxygen. The ionized gas generators are connected to the first molecular sieve. Each one of the ionized gas generators has an outer metal pipe, an inner metal pipe, a dielectric insulating ceramic sheet, and a gas outlet pipe. The outer metal pipe is electrically connected to the low voltage terminal of the power source. The inner metal pipe is electrically connected to the high voltage terminal of the power source. The dielectric insulating ceramic sheet is mounted between the outer metal pipe and the inner metal pipe. An ionizing space is formed between the outer metal pipe and the dielectric insulating ceramic sheet. The gas outlet pipe communicates with the ionizing space. The gas generated by the oil-free gas compressor is capable of flowing sequentially to the first molecular sieve, the ionizing space, and the gas outlet pipe.

The advantages of the present invention are as follows.

First, gas can be purified by the first molecular sieve through chromatography, which is to filter out molecules in the gas except for oxygen, to make a concentration of the oxygen in the gas reach 90% to 93%. Since the purified gas comprises oxygen of sufficient concentration, after the purified gas is passed into the ionized gas generator, high polymers can be produced and oxygen atoms, oxygen molecules, ozone, nitric oxide molecules, and carbon dioxide with low temperature can be generated via pressure purification and ionization. Moreover, further through the multi-channel application of the ionized gas generators, which means using multiple ionized gas generators in parallel connection, sufficient amounts of the aforementioned gases and ions can be generated. Since sufficient amounts of the aforementioned gases and ions are obtained, the aforementioned gases and ions can naturally react to form nitrogen-containing heterocyclic compounds after converged in the gas outlet pipe.

By this, the gas and ions including nitrogen-containing heterocyclic compounds can be blown onto the wound through pressure of the oil-free gas compressor, so that the nitrogen-containing heterocyclic compounds contact the wound, further interact with the water molecular from the wound, and cause Bohr Effect on the wound. Then, the Bohr Effect makes the skin generate sebaceous membranes, thereby quickly healing the wound and helping to naturally restore skin elasticity.

For healing the wound, a user only needs to use the present invention to blow on the wound, which is convenient for the wounded person to use on his/her own. During blowing, the wound is not only disinfected by the ozone, but also quickly healed by the Bohr Effect. Therefore, compared to the conventional wound treatment process, using the present invention to heal the wound avoids secondary infection since change of the dressing is no longer needed, and further avoids tissue fluid sticking, tissue proliferation, and forming scab, thereby effectively reducing the pain during treatment.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
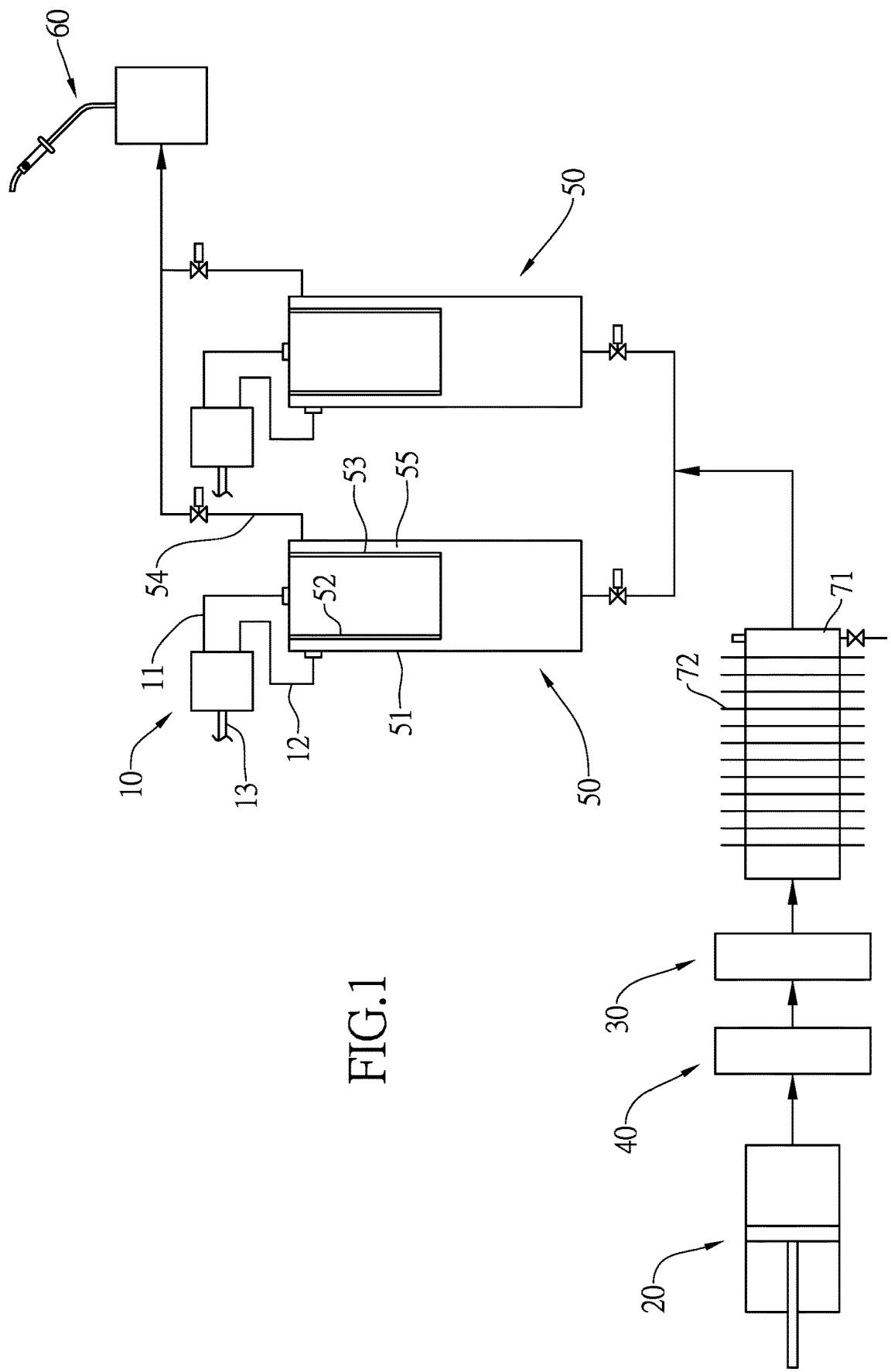
FIG. 1 is a schematic diagram of a device in accordance with the present invention, showing the pipeline configuration.

With reference to FIG. 1, a device in accordance with the present invention comprises a power source 10, an oil-free gas compressor 20, a first molecular sieve 30, a second molecular sieve 40, multiple ionized gas generators 50, and a gas ejecting assembly 60. Besides, in this embodiment, the aforementioned components are connected by a sealed pipe to ensure isolation from the air.

The power source 10 has a high voltage terminal 11 and a low voltage terminal 12. In this embodiment, the power source 10 has a power cable 13 adapted to be connected to a power generator, and supply high voltage via the high voltage terminal 11, and supply low voltage via the low voltage terminal 12. But in other embodiments, the power source 10 can also be implemented as a battery for ease of carriage.

The oil-free gas compressor 20 is a piston type compressor in this embodiment, and generates gas with pressure. The oil-free gas compressor 20 is used to supply pressure to the whole system to be an ejection power source of the gas ejecting assembly 60. Besides, the oil-free gas compressor 20 is capable of pre-drying the gas for pre-disinfection of the following process.

The first molecular sieve 30 is connected to the oil-free gas compressor 20, and is capable of filtering out molecules in the gas generated by the oil-free gas compressor 20 except for oxygen, which is to purify oxygen in the gas through chromatography. Specifically, the first molecular sieve 30 can be a 5 A molecular sieve. Generally, a concentration of oxygen in the air is about 23%, while the concentration of oxygen in the gas passed through the first molecular sieve 30 can reach 90% to 93%.

The second molecular sieve 40 is connected between the oil-free gas compressor 20 and the first molecular sieve 30, and is capable of filtering out water molecule in the gas generated by the oil-free gas compressor 20, which means to dry the gas. Specifically, the second molecular sieve 40 can be a 4 A molecular sieve. The gas generated by the oil-free gas compressor 20 is capable of flowing from the second molecular sieve 40 to the first molecular sieve 30. Therefore, the second molecular sieve 40 can dry the gas completely before the gas enters the first molecular sieve 30, for thorough disinfection.

The ionized gas generators 50 are connected to the first molecular sieve 30. Specifically, multiple ionized gas generators 50 are installed in parallel connection and each of the ionized gas generators 50 is individually connected to the first molecular sieve 30, thereby forming a multi-channel application of the ionized gas generators 50, which allows the first molecular sieve 30 to supply chromatographically purified gas to all of the ionized gas generators 50, in order to generate sufficient gas.

Each of the ionized gas generators 50 has an outer metal pipe 51, an inner metal pipe 52, a dielectric insulating ceramic sheet 53, and a gas outlet pipe 54. The outer metal pipe 51 is electrically connected to the low voltage terminal 12 of the power source 10. The inner metal pipe 52 is electrically connected to the high voltage terminal 11 of the power source 10. The dielectric insulating ceramic sheet 53 is mounted between the outer metal pipe 51 and the inner metal pipe 52, and an ionizing space 55 is formed between the outer metal pipe 51 and the dielectric insulating ceramic sheet 53. The gas is ionized in the ionizing space 55. The gas outlet pipe 54 communicates with the ionizing space 55, and the gas generated by the oil-free gas compressor 20 is capable of flowing sequentially to the first molecular sieve 30, the ionizing space 55, and the gas outlet pipe 54.

Specifically, after the gas with an oxygen concentration about 90% to 93% is fed into the ionized gas generator 50, a corona discharge is applied to the gas with a voltage between 5 KW/V to 8 KW/V. During the corona discharge, negative electrons in the voltage dissociate oxygen molecules in the gas into multiple oxygen atoms, and the oxygen atoms will automatically bond to generate allotropes such as oxygen molecules or ozone under normal temperature and normal pressure. Thus, after the aforementioned ionization process, oxygen atoms, oxygen molecules, ozone, nitric oxide molecules, and carbon dioxide are generated, and further by the multi-channel application of the ionized gas generators 50, sufficient oxygen atoms, oxygen molecules, ozone, nitric oxide molecules, and carbon dioxide can be obtained.

Figure 2:
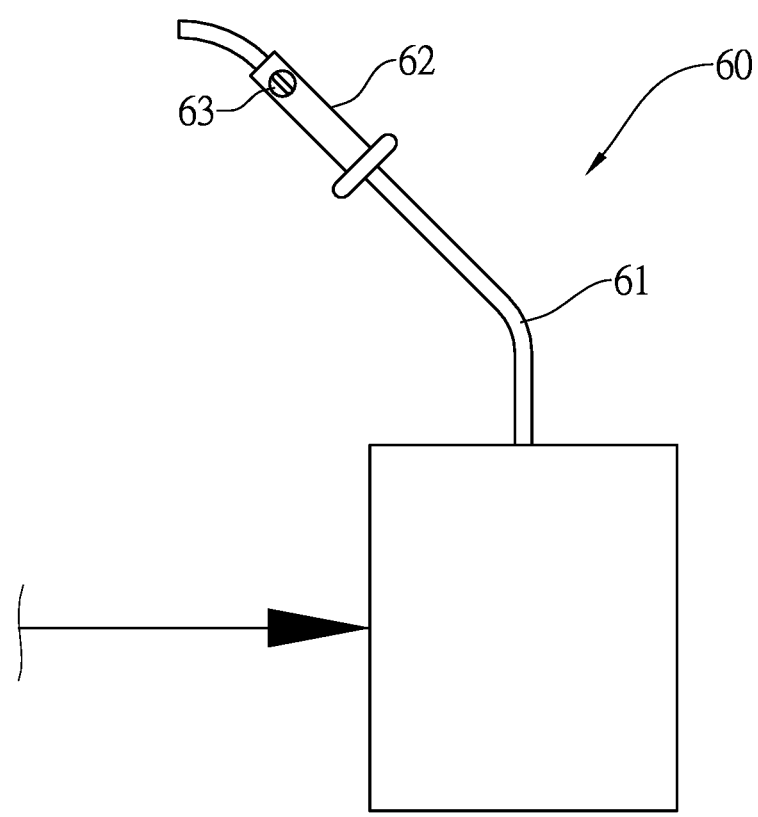
FIG. 2 is a partial enlarged view of the device in FIG. 1, showing the gas ejecting assembly.

With further reference to FIG. 2, the gas ejecting assembly 60 has a connecting pipe 61, a nozzle 62, and a knob 63.

The connecting pipe 61 is connected to the gas outlet pipes 54 of the ionized gas generators 50, which means the gas outlet pipes 54 of the ionized gas generators 50 are converged and are connected to the connecting pipe 61. The connecting pipe 61 is bendable, and specifically, the connecting pipe 61 can be a rubber hose or a metal hose.

The nozzle 62 is mounted on the connecting pipe 61 and has an ejecting opening. The ejecting opening communicates with the connecting pipe 61, and the gas generated by the oil-free gas compressor 20 is capable of flowing from the gas outlet pipes 54 of the ionized gas generators 50 to the connecting pipe 61, and being ejected from the ejecting opening.

By this, a user can hold the nozzle 62 in hand and arbitrarily move the nozzle 62 by the flexibility of the connecting pipe 61 to blow to the wound, so as to be applicable on wounds on any part of the body.

The knob 63 is mounted on the nozzle 62 and is capable of adjusting a diameter of the ejecting opening. Specifically, how the knob 63 adjusts the diameter of the ejecting opening can be the same as how the water-tap adjusts the water flow.

Since the whole system is sealed, after the opening of the nozzle 62 is opened, the pressure supplied by the oil-free gas compressor 20 becomes a power source for ejecting the ionized gas. Besides, because the ejecting speed of the gas is affected by the diameter of the ejecting opening, the knob 63 is used to adjust the ejecting speed and the ejecting force of the gas ejection to control the ejecting speed and the ejecting force within an appropriate range. Therefore, the ejecting speed and the ejecting force can be controlled to match different situations, which is beneficial to wound healing and skin elasticity recovery.

After sufficient oxygen atoms, oxygen molecules, ozone, nitric oxide molecules, and carbon dioxide are converged at a connecting point of the gas outlet pipes 54 and the connecting pipe 61, those atoms and molecules will naturally react to form nitrogen-containing heterocyclic compounds, and therefore the gas in the gas ejecting assembly 60 comprises the aforementioned atoms and molecules and the nitrogen-containing heterocyclic compounds. Thus, after the ejecting opening is opened, the aforementioned atoms and molecules and the nitrogen-containing heterocyclic compounds are ejected by the pressure of the oil-free gas compressor 20, and then the user can blow the aforementioned atoms and molecules and the nitrogen-containing heterocyclic compounds on the wound.

Additionally, in this embodiment, the device further has an air storage tank 71 and multiple heat sinks 72. The air storage tank 71 is connected between the first molecular sieve 30 and the parallel connected ionized gas generators 50. The heat sink 72 is mounted on an outer surface of the air storage tank 71. With the air storage tank 71 and the heat sinks 72, the gas passed through the first molecular sieve 30 can be stored and cooled down. Nevertheless, the air storage tank 71 and the heat sinks 72 can be replaced by a cooling coil in other embodiments, or the device can also be implemented without the air storage tank 71 and the heat sinks 72.

Furthermore, in order to reduce bacteria in the abovementioned gas, a nano silver fiber (not shown in figures) can also be installed in front of the first molecular sieve 30 to pre-filter and pre-sterilize the gas.

When in use, gas is compressed by the oil-free gas compressor 20 first, and is transferred to the second molecular sieve 40 to be dried next, and then passes through the first molecular sieve 30 and is purified by chromatography to make the concentration of the oxygen reach 90% to 93%. Next, the gas with high oxygen concentration will be sent into the parallel connected ionized gas generators 50 to ionize the gas in the ionizing space 55 to generate oxygen atoms, oxygen molecules, ozone, nitric oxide molecules, and carbon dioxide. At last, after the gas processed by all of the ionized gas generators 50 is converged, nitrogen-containing heterocyclic compounds can be naturally generated in the gas ejecting assembly 60. By this, the user can open the ejecting opening of the gas ejecting assembly 60 and adjust the ejecting speed and the ejecting force by the knob 63 to an appropriate range to blow the processed gas to the wound.

The advantages of the present invention are as follows.

First, the gas can be purified by the first molecular sieve 30 through chromatography, which is to filter out molecules in the gas except for oxygen, to make the oxygen concentration in the gas reach 90% to 93%. Since the purified gas comprises oxygen of sufficient concentration, after the purified gas is passed into the ionized gas generator 50, high polymers can be produced and oxygen atoms, oxygen molecules, ozone, nitric oxide molecules, and carbon dioxide with low temperature can be generated via pressure purification and ionization. Moreover, further through the multi-channel application of the ionized gas generators 50, which means to use the multiple ionized gas generators 50 in parallel connection, sufficient amounts of the aforementioned gases and ions can be generated. Since sufficient amounts of the aforementioned gases and ions are obtained, the aforementioned gases and ions can naturally react to form nitrogen-containing heterocyclic compounds after converged in the gas outlet pipe 54.

By this, the gas and ions including nitrogen-containing heterocyclic compounds can be blown onto the wound through pressure of the oil-free gas compressor 20, so that the nitrogen-containing heterocyclic compounds contact the wound, further interact with the moisture from the wound, and cause Bohr Effect on the wound. Then, the Bohr Effect makes the skin generate sebaceous membrane, thereby quickly healing the wound and assisting in naturally restoring skin elasticity.

For healing the wound, the user only needs to use the present invention to blow on the wound, which is convenient for the wounded person to use on his/her own. During blowing, the wound is not only disinfected by the ozone, but also quickly healed by the Bohr Effect. Therefore, using the present invention to heal the wound avoids secondary infection since change of the dressing is no longer needed, and further avoids tissue fluid sticking, tissue proliferation, and scab formation, thereby effectively reducing the pain during treatment.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A device for generating high polymer low temperature ionized gas to promote wound healing; the device comprising:
   a power source having
      a high voltage terminal; and
      a low voltage terminal;
   an oil-free gas compressor generating gas with pressure;
   a first molecular sieve connected to the oil-free gas compressor; the first molecular sieve being capable of filtering out molecules in the gas generated by the oil-free gas compressor except for oxygen; and
   multiple ionized gas generators connected to the first molecular sieve; each one of the ionized gas generators having
      an outer metal pipe electrically connected to the low voltage terminal of the power source;
      an inner metal pipe electrically connected to the high voltage terminal of the power source;
      a dielectric insulating ceramic sheet mounted between the outer metal pipe and the inner metal pipe; an ionizing space formed between the outer metal pipe and the dielectric insulating ceramic sheet; and
      a gas outlet pipe communicating with the ionizing space; the gas generated by the oil-free gas compressor being capable of flowing sequentially to the first molecular sieve, the ionizing space, and the gas outlet pipe.

2. The device for generating high polymer low temperature ionized gas to promote wound healing as claimed in claim 1, wherein the first molecular sieve is a 5 A molecular sieve.

3. The device for generating high polymer low temperature ionized gas to promote wound healing as claimed in claim 1, wherein the device further has
   a second molecular sieve connected between the oil-free gas compressor and the first molecular sieve; the second molecular sieve being capable of filtering out water molecule in the gas generated by the oil-free gas compressor; the gas generated by the oil-free gas compressor being capable of flowing from the second molecular sieve to the first molecular sieve.

4. The device for generating high polymer low temperature ionized gas to promote wound healing as claimed in claim 2, wherein the device further has
   a second molecular sieve connected between the oil-free gas compressor and the first molecular sieve; the second molecular sieve being capable of filtering out water molecule in the gas generated by the oil-free gas compressor; the gas generated by the oil-free gas compressor being capable of flowing from the second molecular sieve to the first molecular sieve.

5. The device for generating high polymer low temperature ionized gas to promote wound healing as claimed in claim 3, wherein the second molecular sieve is a 4 A molecular sieve.

6. The device for generating high polymer low temperature ionized gas to promote wound healing as claimed in claim 4, wherein the second molecular sieve is a 4 A molecular sieve.

7. The device for generating high polymer low temperature ionized gas to promote wound healing claimed in claim 1, wherein the device further has
   a gas ejecting assembly having
      a connecting pipe connected to the gas outlet pipe of the ionized gas generators; the connecting pipe being bendable; and
      a nozzle mounted to the connecting pipe and having
         an ejecting opening communicating with the connecting pipe; the gas generated by the oil-free gas compressor being capable of flowing from the gas outlet pipes of the ionized gas generators to the connecting pipe, and being ejected from the ejecting opening.

8. The device for generating high polymer low temperature ionized gas to promote wound healing claimed in claim 6, wherein the device further has
   a gas ejecting assembly having
      a connecting pipe connected to the gas outlet pipe of the ionized gas generators; the connecting pipe being bendable; and
      a nozzle mounted to the connecting pipe and having
         an ejecting opening communicating with the connecting pipe; the gas generated by the oil-free gas compressor being capable of flowing from the gas outlet pipes of the ionized gas generators to the connecting pipe, and being ejected from the ejecting opening.

9. The device for generating high polymer low temperature ionized gas to promote wound healing as claimed in claim 7, wherein the gas ejecting assembly further has
   a knob mounted on the nozzle and being capable of adjusting a diameter of the ejecting opening.

10. The device for generating high polymer low temperature ionized gas to promote wound healing as claimed in claim 8, wherein the gas ejecting assembly further has
   a knob mounted on the nozzle and being capable of adjusting a diameter of the ejecting opening.

* * * * *